United States Patent [19]

Mahieu et al.

[11] Patent Number: 4,676,263

[45] Date of Patent: Jun. 30, 1987

[54] PROCESS AND COMPOSITION FOR SETTING THE HAIR

[75] Inventors: Claude Mahieu, Paris; Christos Papantoniou, Montmorency, both of France

[73] Assignee: Societe Anonyme dite: L' Oreal, Paris, France

[21] Appl. No.: 512,673

[22] Filed: Jul. 11, 1983

[30] Foreign Application Priority Data

Jul. 13, 1982 [FR] France ............................ 82 12298

[51] Int. Cl.$^4$ ........................... A61K 7/06; A61K 7/09
[52] U.S. Cl. ........................................ 132/7; 424/70; 424/71; 424/72; 424/81; 424/DIG. 2
[58] Field of Search ................ 132/7; 424/47, 70, 71, 424/72, 81

[56] References Cited

U.S. PATENT DOCUMENTS

| 2,390,073 | 12/1945 | Calva | 167/87.1 |
|---|---|---|---|
| 3,820,550 | 6/1974 | Kinney et al. | 132/7 |
| 3,934,595 | 1/1976 | Madrange nee Dermain et al. | 424/DIG. 2 |
| 3,946,749 | 3/1976 | Papantoniou | 424/DIG. 1 |
| 4,172,887 | 10/1979 | Vanlerberghe et al. | 424/70 |
| 4,189,468 | 2/1980 | Vanlerberghe et al. | 424/DIG. 1 |
| 4,524,787 | 6/1985 | Khalil et al. | 132/7 |

FOREIGN PATENT DOCUMENTS

| 2368508 | 6/1978 | France | 424/70 |
|---|---|---|---|
| 2417981 | 10/1979 | France | 424/70 |
| 1301902 | 1/1973 | United Kingdom | 132/7 |
| 2014584 | 8/1979 | United Kingdom | 132/7 |

Primary Examiner—Andrew H. Metz
Assistant Examiner—Helane Myers
Attorney, Agent, or Firm—Cushman, Darby & Cushman

[57] ABSTRACT

A composition and process for setting hair comprises impregnating the hair with a composition containing in solution in a cosmetic vehicle at least one water-soluble polymer containing at least 5% of units having a primary amide function, a crosslinking agent and an acid catalyst. The hair is then placed on hair-setting rollers and dried by means of an external heat source. The hair rollers are then removed.

18 Claims, No Drawings

PROCESS AND COMPOSITION FOR SETTING THE HAIR

The present invention relates to a new process for treating hair and more particularly to a process for setting the hair as well as to a hair-setting composition.

Hair setting lotions or compositions essentially comprise an aqueous or hydroalcoholic solution of a resin, which is applied to the hair. After application of the composition, the hair, placed on rollers, is dried. Thereafter, the rollers are removed.

Resins generally used in these compositions can be natural resins or, more currently, synthetic polymers whose properties must result in a good holding of the hair set, that is to say, have a slight or weak absorption of humidity so as not to render the hair sticky, or to provoke the formation of resin flakes. The resin at the same time should impart to the hair a shiny appearance and facilitate its combing or disentanglement.

Various polymers or resins have already been proposed for use in such hair setting compositions and on the whole these known polymers provide satisfactory results.

However, it has now been observed that a particularly perceptible improvement of the hair setting properties, principally, a better hold between successive shampoos can be obtained by using certain types of polymers and by crosslinking these polymers on the hair.

Such crosslinking improves the various sought-after properties and especially a long lasting hold or set, ease of combing the hair, an absence of resin or polymer powdering when the hair is brushed or combed as well as hair liveliness and shininess.

The present invention thus relates to a new process for setting the hair which achieves these desirable objectives, the said process comprising impregnating the hair with a composition containing, in solution in an appropriate cosmetic vehicle, at least one water-soluble polymer containing at least 5%, and preferably 10-100%, of units having a primary amide function, a crosslinking agent and an acid catalyst, placing the hair on hair setting rollers, drying the hair by contacting it with an external heat source and removing the said hair setting rollers.

Representative preferred water-soluble polymers capable of being used in the process according to the present invention, include the following polymers:

(1) a copolymer having the formula $$\left[\begin{array}{c} R_1 \\ | \\ -CH-CH- \\ | \\ CONH_2 \end{array}\right] \ldots \left[\begin{array}{c} R_4 \\ | \\ -CH_2-C- \\ | \\ R_3 \end{array}\right] \quad (I)$$

$$\quad (a) \quad\quad\quad (b)$$

wherein:
$R_1$ and $R_2$ represent hydrogen or methyl with the proviso that $R_1$ and $R_2$ cannot simultaneously represent methyl,
$R_3$ represents a member selected from the group consisting of
(i) $-CO-Z-(CH_2)_y-R_5$, wherein Z represents $-NH-$ or $-O-$, y is 2 or 3 and $R_5$ is $$-N\begin{array}{c} CH_3 \\ \diagdown \\ \diagup \\ CH_3 \end{array} \quad \text{or} \quad -\overset{\oplus}{N}\begin{array}{c} CH_3 \\ \diagdown \\ -CH_3 \; X^{\ominus} \\ \diagup \\ R_6 \end{array}$$

wherein $R_6$ is alkyl having 1-4 carbon atoms and X represents Cl, Br, I or $OSO_3CH_3$,
(ii) $-CO-Z-(CH_2)_t-CH_3$, wherein Z has the meaning given above and t is a whole number ranging from 0 to 17 inclusive,
(iii) $-CN$,
(iv) $-COOH$,
(v) $-CH=O$,
(vi)

$$-N\diagup\!\!\diagdown_{\underset{O}{\overset{\|}{\phantom{C}}}}$$

and
(vii) $-C_6H_5$,
$R_4$ represents hydrogen or methyl when $R_3$ represents (i) to (iv), or $R_4$ represents only hydrogen when $R_3$ represents (v) to (vii),
the (a) unit representing from 5 to 100% of the total units in the polymer and preferably from 8 to 70% and
the (b) unit representing from 95 to 0% of the total units in the polymer and preferably from 30 to 82%, the units (a)+(b) being equal to 100%.

Representative monomers capable of providing units I(a) include acrylamide, methacrylamide and crotonamide.

Representative monomers capable of providing units I(b) include 2-N,N-dimethylamino ethyl methacrylate, butyl methacrylate, octyl methacrylate, dodecyl methacrylate and octadecyl methacrylate as well as the corresponding acrylates, methacrylamides and acrylamides, acrylonitrile, acrylic acid, methacrylic acid, acrolein, N-vinylpyrrolidone and styrene.

Copolymers of this type can be bi-, tri-, tetra- or higher copolymers. Representative copolymers of formula (I) which can be used in accordance with the present invention include, in particular, those described in French Pat. No. 71/03017;
(2) a cyclopolymer having the formula $$\left[\begin{array}{c} R_1 \; R_2 \\ | \; \; | \\ -CH-C- \\ | \\ CONH_2 \end{array}\right] \ldots \left[\begin{array}{c} CH_2 \\ \diagup \; \diagdown \\ -CH \quad\quad CH- \\ | \quad\quad\quad | \\ CH_2 \quad CH_2 \\ \diagdown \; \diagup \\ \overset{\oplus}{N} \; A^{\ominus} \\ \diagup \; \diagdown \\ R_7 \quad R_8 \end{array}\right] \quad (II)$$

$$\quad (a') \quad\quad\quad\quad (b')$$

wherein:
$R_1$ and $R_2$ have the same meaning as given above in the definition of the polymer of formula (I),
$R_7$ and $R_8$ each independently represent alkyl having 1-12 carbon atoms or hydroxyalkyl having 2-3 carbon atoms, A represents Cl, Br, I or OSO₃CH₃,
the (b') unit represents 95-5% of the total units in the polymer and preferably 92-30%,
the units (a') and (b') being equal to 100 percent.

The cyclopolymers of this type are more particularly described in French Pat. No. 73.23970; and (3) polymers of poly-β-alanine type resulting from the anionic polymerization of crotonamide, acrylamide or methacrylamide, these polymers having the formula

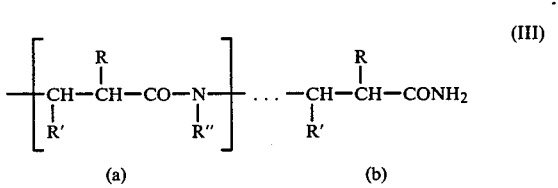

(III)

wherein
R and R' represent hydrogen or methyl,
R" represents hydrogen or a branching of the formula:

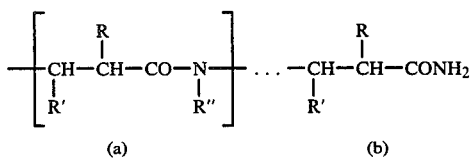

the percentage of terminal primary amide units (b) being between 5 and 35 percent relative to the total of the amide units of the polymer.

The preparation of these poly-β-alanine type polymers is described in U.S. Pat. Nos. 2,749,331 and 4,082,730.

Polymers other than those mentioned above can also be used in the compositions according to the present invention. Representative ones of these other polymers include, in particular, those described in French Pat. Nos. 76.30886, 77.10220, 77.15088 and 78.27074. These other polymers have a structure which corresponds to the preceding definition, that is to say, polymers containing at least 5% of units having a primary amide function.

Generally, the polymers used in the process according to the present invention have a molecular weight ranging between 500 and about 200,000, preferably between 2,000 and 100,000 (the molecular weight being determined by the light diffusion method).

Although the impregnation of the hair can be carried out in several stages, for example, by application in a first stage of a solution containing the polymer and the crosslinking agent and the application in a second stage of a solution of the acid catalyst, it is preferable, so as to obtain a good impregnation and a satisfactory result, to prepare the impregnation composition at the time of use, that is to say, by admixing in a cosmetic carrier the polymer, the crosslinking agent and the acid catalyst.

The cosmetic carrier is, preferbly, water or a hydroalcoholic solution of a lower aliphatic alcohol, such as ethanol or isopropanol.

The impregnation composition, although soluble at ambient temperature, should be applied to the hair as soon as the acid catalyst has been introduced into the admixture so as to avoid any significant premature onset of the crosslinking reaction.

Representative crosslinking agents usefully employed in the present invention include glyoxal, glutaraldehyde and formaldehyde, as well as compounds capable of liberating formaldehyde such as dimethylolurea or thiourea, dimethylol ethylene urea or thioeurea and trimethylolmelamine.

The acid catalyst is preferably an organic or mineral acid such as hydrochloric acid, oxalic acid and the like, the catalyst being present in the hair setting composition, in an amount sufficient so as to impart to the final impregnation composition a pH between 1 and 2. Optionally there can be employed with the organic or mineral acid a mineral salt such as potassium chloride.

After impregnation of the hair using a sufficient amount of the composition of the present invention, which amount can be a function of the amount of the hair being impregnated, although that amount is generally between about 5 and 100 cc, the hair is then wound or rolled on hair setting rollers having a diameter which can vary between about 10 and 50 mm.

Once this operation is completed, the hair is then dried at a temperature of about 40° to 65° C. for a period of time ranging from about 15 to 90 minutes, this drying operation having the effect of initiating and completing the crosslinking reaction of the polymer.

After drying the hair, the rollers are then removed and the hair is given a final combing.

Tests measuring the holding power of the curls or waves obtained by the hair setting process of the present invention in an atmosphere of controlled humidity and temperature, have shown that the curls exhibit better retention than those obtained with conventional hair setting compositions.

The present invention also relates to a composition for use in the process of the present invention, this composition being packaged in several parts which are to be mixed at the moment of use. The final composition, after admixture of the various parts, contains in an aqueous or hydroalcoholic solution the above defined polymer in an amount ranging from 0.1 to 5 weight percent, the aforementioned crosslinking agent in an amount between 4 and 30 percent by weight relative to the weight of the polymer in said composition and the said acid catalyst in an amount sufficient to provide a pH between 1 and 2.

According to the first embodiment, the composition of the present invention is provided in the form of a two-part package.

In accordance with one variation of this first embodiment, the first part comprises an aqueous or hydroalcoholic solution of the polymer and the crosslinking agent, and the second part comprises the acid catalyst.

The pH of the first part of the composition is generally between 5-8, preferably close to neutral.

In accordance with a second variation of this first embodiment, the first part comprises an aqueous or hydroalcoholic solution of the polymer at an acid pH (pH between 1 and 2), and the second part comprises an aqueous or hydroalcoholic solution of the crosslinking agent also at an acid pH (again generally about 1-2).

According to a second embodiment of the invention, the composition is provided in the form of a three-part package, the first part comprising an aqueous or hydroalcoholic solution of the polymer, the second part comprising an aqueous or hydroalcoholic solution of the crosslinking agent and the third part comprising an aqueous solution of the acid catalyst.

The polymer solutions can also contain other conventional hair setting lotion adjuvants. Among these adjuvants are, in particular, perfumes, coloring agents, preservatives, softening agents and the like.

The following non-limiting examples illustrate the present invention.

EXAMPLE 1

(a) 2-part package

A hair setting composition is packaged in the following two-parts which are to be mixed at the moment of use.

| 1st Part | |
|---|---|
| Poly-β-alanine (having 17% of primary amide terminal units) | 1 g |
| Glutaraldehyde | 0.1 g |
| Perfume | 0.05 g |
| Water, sufficient amount for the pH of this solution is 6 | 100 g |
| 2nd Part | |
| 2.1 cc of 1 N HCl solution | |

(b) Hair setting process

At the moment of use the said second part is introduced with stirring into the first part. The pH of the resulting composition is 2.

As soon as the mixture has been effected the composition is applied to the hair after which the hair is rolled up on hair curlers having a diameter of 15 mm.

After drying the hair under a hood at a temperature of 60° C. for about 30 minutes, the rollers are removed and the hair is combed.

The resulting curls have a long lasting hold, the hair combs easily and is soft to the touch.

EXAMPLES 2-6

(a) 2-part package

EXAMPLE 2

| 1st Part | |
|---|---|
| 0.2 N KCl solution | 25 ml |
| 0.2 N HCl solution | 67 ml |
| Poly-β-alanine (having 17% primary amide terminal units) | 1 g |
| 2nd Part | |
| 0.2 N KCl solution | 25 ml |
| 0.2 N HCl solution | 67 ml |
| Glutaraldehyde | 0.07 g |

EXAMPLE 3

| 1st Part | |
|---|---|
| 0.2 N KCl solution | 25 ml |
| 0.2 N HCl solution | 67 ml |
| Poly-β-alanine (having 30% primary amide terminal units) | 9 g |
| 2nd Part | |
| 0.2 N KCl solution | 25 ml |
| 0.2 N HCl solution | 67 ml |
| Glutaraldehyde | 0.36 g |

EXAMPLE 4

| 1st Part | |
|---|---|
| 0.2 N KCl solution | 25 ml |
| 0.2 N HCl solution | 67 ml |
| Poly-β-alanine (having 17% primary amide terminal units) | 0.4 g |
| 2nd Part | |
| 0.2 N KCl solution | 25 ml |
| 0.2 N HCl solution | 67 ml |
| Glutaraldehyde | 0.12 g |

EXAMPLE 5

| 1st Part | |
|---|---|
| 0.2 N KCl solution | 27 ml |
| 0.2 N HCl solution | 73 ml |
| Poly-β-alanine (having 17% primary amide terminal units) | 1 g |
| 2nd Part | |
| 0.2 N KCl solution | 27 ml |
| 0.2 N HCl solution | 73 ml |
| Glutaraldehyde | 0.07 g |

EXAMPLE 6

| 1st Part | |
|---|---|
| 0.2 N KCl solution | 100 ml |
| 0.2 N HCl solution | 26 ml |
| Poly-β-alanine (having 17% primary amide terminal units) | 0.8 g |
| 2nd Part | |
| 0.2 N KCl solution | 100 ml |
| 0.2 N HCl solution | 26 ml |
| Glutaraldehyde | 0.08 g |

(b) Hair setting process.

At the moment of use the two parts in each of Examples 2-6 above are mixed together, and the resulting compositions are applied to the hair.

The hair is then rolled up on hair setting rollers having a diameter of about 15 mm. The hair is dried under a hood at 60° C. for about 45 minutes.

The resulting curls have a long lasting hold, the hair combs easily and is soft to the touch.

EXAMPLE 7

(a) 2-part package

A hair setting composition is packaged in the following two parts which are mixed at the moment of use.

| 1st Part | |
|---|---|
| Copolymer of 5% acrylamide/ 95% N,N—dimethyl,N,N— diallylammonium chloride (French patent No. 73.23970) | 1.5 g |
| Glutaraldehyde | 0.15 g |
| Perfume | 0.08 g |
| Water, sufficient amount for | 100 g |
| 2nd Part | |
| 2.1 cc of 1 N HCl solution | |

(b) Hair setting process

At the moment of use the second part, above, is introduced with stirring into the first part.

The resulting mixture is then applied to the hair after which the hair is rolled upon rollers having a diameter of 15 mm.

The hair is then dried under a hood at about 50° C. for 20 minutes and the rollers are removed. The resulting curls have an excellent hold, principally in a humid atmosphere.

EXAMPLE 8

(a) 2-part package

A hair setting composition is packaged in the following two parts which are mixed at the moment of use.

| 1st Part | |
|---|---|
| Copolymer of 68% N—vinylpyrrolidone/ 8% acrylamide/8% acrylic acid/ 8% 2-N,N—dimethylamino ethyl methacrylate/ 8% 2-N,N—dimethylamino ethyl methacrylate quaternized with dimethyl sulfate (French patent No. 71.03017) | 1 g |
| Glutaraldehyde | 0.1 g |
| Perfume | 0.07 g |
| Water, sufficient amount for | 100 g |
| 2nd Part | |
| 2.1 cc of HCl solution | |

(b) Hair setting process

At the moment of use the second part is admixed with the first part with stirring.

After having effected this admixture the composition is then applied to the hair which is then rolled up on rollers.

After drying the hair under a hood the rollers are removed and the hair is given a final combing.

The resulting curls have an excellent hold and the hair is shiny and soft to the touch.

What is claimed is:

1. A process for setting the hair comprising impregnating the hair with a composition comprising an aqueous or hydroalcoholic solution of at least one water-soluble polymer containing 10-100 percent units having a primary amide function, a crosslinking agent and an acid catalyst, placing the hair on hair setting rollers, drying the hair by means of an external heat source whereby the crosslinking of said polymer is completed on the hair and removing said hair setting rollers, said crosslinking agent being glyoxal, glutaraldehyde, formaldehyde or a compound capable of liberating formaldehyde, said compound being selected from the group consisting of dimethylolurea or thiourea, dimethylol ethylene urea or thiourea and trimethylolmelamine.

2. The process of claim 1 wherein said water-soluble polymer contains from 10-100% of units having a primary amide function.

3. The process of claim 1 wherein said water-soluble polymer has the formula $$\left[ \begin{array}{c} R_1 \; R_2 \\ | \; | \\ -CH-C- \\ | \\ CONH_2 \end{array} \right] \ldots \left[ \begin{array}{c} R_4 \\ | \\ -CH_2-C- \\ | \\ R_3 \end{array} \right] \quad (I)$$

(a) (b)

wherein:

$R_1$ and $R_2$ represent hydrogen or methyl with the proviso that $R_1$ and $R_2$ are not simultaneously methyl, $R_3$ represents a member selected from the group consisting of (i) —CO—Z—$(CH_2)_y$—$R_5$, wherein Z represents —NH— or —O—, y is 2 or 3 and $R_5$ is $$-N\begin{array}{c}CH_3\\CH_3\end{array} \quad \text{or} \quad -\overset{\oplus}{N}\begin{array}{c}CH_3\\CH_3\\R_6\end{array} X^{\ominus}$$

wherein $R^6$ is alkyl having 1-4 carbon atoms and X represents Cl, Br, I or $OSO_3CH_3$, (ii) —CO—Z—$(CH_2)_t$—$CH_3$, wherein Z has the meaning given above and t is a whole number ranging from 0 to 17 inclusive, (iii) —CN, (iv) —COOH, (v) —CH=O, (vi)

$$-N\underset{O}{\overset{\displaystyle\frown}{\underset{\|}{\phantom{X}}}}$$

and (vii) —$C_6H_5$, $R_4$ represents hydrogen or methyl when $R_3$ represents (i) to (iv) above, or $R_4$ represents only hydrogen when $R_3$ represents (v) to (vii), above, the (a) units representing from 5 to 100% and the (b) units from 95 to 0%, the units (a)+(b) being equal to 100%.

4. The process of claim 1 wherein said water-soluble polymer is a cyclopolymer having the formula $$\left[ \begin{array}{c} R_1 \; R_2 \\ | \; | \\ -CH-C- \\ | \\ CONH_2 \end{array} \right] \ldots \left[ \begin{array}{c} CH_2 \\ / \; \backslash \\ -CH \quad CH- \\ | \quad\quad | \\ CH_2 \quad CH_2 \\ \backslash \overset{\oplus}{N} / \quad A^{\ominus} \\ / \; \backslash \\ R_7 \quad R_8 \end{array} \right] \quad (II)$$

(a') (b')

wherein:

$R_1$ and $R_2$ represent hydrogen or methyl with the proviso that $R_1$ and $R_2$ are not simultaneously methyl, $R_7$ and $R_8$ each independently represent alkyl having 1-12 carbon atoms or hydroxyalkyl having 2-3 carbon atoms, A represents Cl, Br, I or $OSO_3H$, the (a') units representing from 5-95%, and the (b') units representing from 95-5%, the units (a')+(b') being equal to 100%.

5. The process of claim 1 wherein said water-soluble polymer is a poly-$\beta$-alanine type polymer having the formula

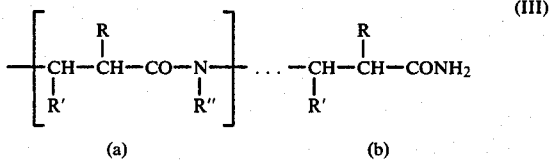

wherein:
R and R' represent hydrogen or methyl, and
R" represents hydrogen or a branching of the formula

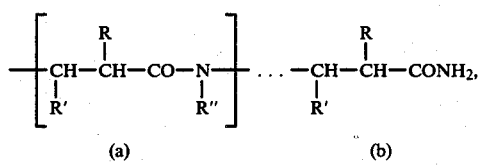

the percentage of primary amide terminal units (b) being between 5 and 35 percent relative to the total units of the polymer.

6. The process of claim 1 wherein said water-soluble polymer has a molecular weight ranging from 500 to about 200,000.

7. The process of claim 1 wherein said water-soluble polymer has a molecular weight ranging from 2,000 to 100,000.

8. The process of claim 1 wherein said acid catalyst is an organic or mineral acid.

9. The process of claim 8 wherein said acid catalyst is hydrochloric acid or oxalic acid.

10. The process of claim 1 wherein drying the hair is carried out at a temperature ranging from about 40° to 65° C. for a period of time ranging from about 15 to 90 minutes.

11. A process for setting the hair comprising impregnating the hair with a composition comprising an aqueous or hydroalcoholic solution of (1) a water-soluble polymer selected from the group consisting of poly-β-alanine having 17% primary amide terminal units, poly-β-alanine having 30% primary amide terminal units, a copolymer of 5% acrylamide and 95% N,N-dimethyl-N,N-diallylammonium chloride and a copolymer of 68% N-vinyl pyrrolidone, 8% acrylamide, 8% acrylic acid, 8% 2-N,N-dimethylamino ethyl methacrylate and 8% 2-N,N-dimethylamino ethyl methacrylate quaternized with dimethyl sulfate, (2) glutaraldehyde as a crosslinking agent, and (3) an acid catalyst, placing the hair on hair setting rollers, drying the hair by means of an external heat source whereby the crosslinking of said polymer is completed on the hair and removing said hair setting rollers.

12. A hair setting composition packaged in two or more parts to be mixed at the time to use, said composition on admixture of said parts comprising an aqueous or hydroalcoholic solution of a water-soluble polymer containing 10–100 percent of units having a primary amide function in an amount ranging from 0.1 to 5 weight percent of said composition, a crosslinking agent in an amount ranging from 4 to 30 weight percent based on the weight of said water-soluble polymer and acid catalyst in an amount sufficient to impart to said composition a pH ranging from 1 to 2, said crosslinking agent being glyoxal, glutaraldehyde, formaldehyde or a compound capable of liberating formaldehyde, said compound being selected from the group consisting of dimethylolurea or thiourea, dimethylol ethylene urea or thiourea and trimethylolmelamine.

13. The hair setting composition of claim 12 packaged in two parts, wherein a first part comprises an aqueous or hydroalcoholic solution of said polymer and said crosslinking agent and a second part comprises said acid catalyst.

14. The hair setting composition of claim 13 wherein said first part has a pH ranging from 5 to 8.

15. The hair setting composition of claim 12 packaged in two parts wherein a first part comprises an aqueous or hydroalcoholic solution of said polymer at an acid pH and a second part comprises an aqueous or hydroalcoholic solution of said crosslinking agent at an acid pH.

16. The hair setting composition of claim 12 packaged in three parts wherein a first part comprises an aqueous or hydroalcoholic solution of said polymer, a second part comprises an aqueous or hydroalcoholic solution of said crosslinking agent and a third part comprises an aqueous solution of said acid catalyst.

17. The hair setting composition of claim 12, wherein the aqueous or hydroalcoholic solution of said polymer also contains an effective amount of one or more of a perfume, a coloring agent, a preservative or a softening agent.

18. A hair setting composition packaged in two or more parts to be mixed at the time of use, said composition on admixture of said parts comprising an aqueous or hydroalcoholic solution of (1) a water-soluble polymer selected from the group consisting of poly-β-alanine having 17% primary amide terminal units, poly-β-alanine having 30% primary amide terminal units, a copolymer of 5% acrylamide and 95% N,N-dimethyl-N,N-diallylammonium chloride and a copolymer of 68% N-vinyl pyrrolidone, 8% acrylamide, 8% acrylic acid, 8% 2,-N,N-dimethylamino ethyl methacrylate and 8% 2-N,N-methylamino ethyl methacrylate quaternized with dimethyl sulfate, said water-soluble polymer being present in an amount ranging from 0.1 to 5 weight percent of said composition, (2) glutaraldehyde as a crosslinking agent, present in an amount ranging from 4 to 30 weight percent based on the weight of said water-soluble polymer amd (3) an acid catalyst in an amount sufficient to impart to said composition a pH ranging from 1 to 2.

* * * * *